United States Patent [19]

Kormany et al.

[11] 4,061,860

[45] Dec. 6, 1977

[54] STILBENE COMPOUNDS

[75] Inventors: Géza Kormány, Allschwil; Guglielmo Kabas, Aesch; Hans Schläpfer; Adolf Emil Siegrist, both of Basel, all of Switzerland

[73] Assignee: Ciba-Geigy Corporation, Ardsley, N.Y.

[21] Appl. No.: 601,881

[22] Filed: Aug. 6, 1975

[30] Foreign Application Priority Data

Aug. 14, 1974 Switzerland .................. 11108/74

[51] Int. Cl.$^2$ .................................... C07D 413/10
[52] U.S. Cl. ........................... 542/462; 252/301.24; 252/301.27; 252/301.28; 252/301.29; 542/464
[58] Field of Search ....... 260/240 C, 240 CA, 240 D, 260/308 A

[56] References Cited

U.S. PATENT DOCUMENTS

| | | | |
|---|---|---|---|
| 3,697,513 | 10/1972 | Siegrist ........................ | 260/240 D |
| 3,725,395 | 4/1973 | Siegrist et al. ............... | 260/240 CA |
| 3,732,221 | 5/1973 | Siegrist et al. ............... | 260/240 C |
| 3,796,705 | 3/1974 | Siegrist ........................ | 260/240 C |
| 3,819,615 | 6/1974 | Siegrist ........................ | 260/240 C |
| 3,830,848 | 8/1974 | Siegrist ........................ | 260/240 CA |
| 3,843,633 | 10/1974 | Weber et al. ................. | 260/240 C |
| 3,891,632 | 6/1975 | Fleck et al. ................... | 260/240 D |
| 3,901,883 | 8/1975 | Liechti et al. ................ | 260/240 D |

FOREIGN PATENT DOCUMENTS 2,262,340 6/1973 Germany.
2,025,792 10/1970 Germany.

OTHER PUBLICATIONS

Dorlars et al., Chem. Abstracts, 1969 (71) No. 126001.
Okada et al., Chem. Abstracts, 1969 (71) No. 126004.

*Primary Examiner*—Arthur P. Demers
*Attorney, Agent, or Firm*—Edward McC. Roberts; Prabodh I. Almaula

[57] ABSTRACT

Stilbene compounds of the formula

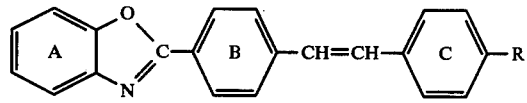

wherein R denotes the radical

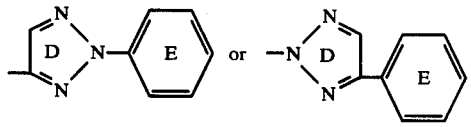

and wherein the rings A, B, C, D and E can carry non-chromophoric substituents are useful for the optical brightening of organic materials.

18 Claims, No Drawings

STILBENE COMPOUNDS

SUMMARY OF THE INVENTION

The present invention relates to new stilbene compounds, processes for their manufacture and their use for the optical brightening of high molecular organic materials.

The new stilbene compounds correspond to the formula

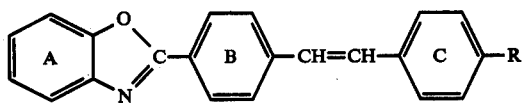

wherein R denotes the radical

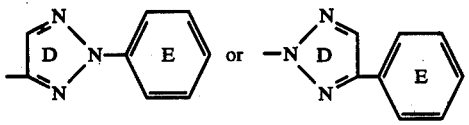

and wherein the rings A, B, C, D and E can carry non-chromophoric substituents.

Accordingly, the formula (1) comprises compounds of the formulae

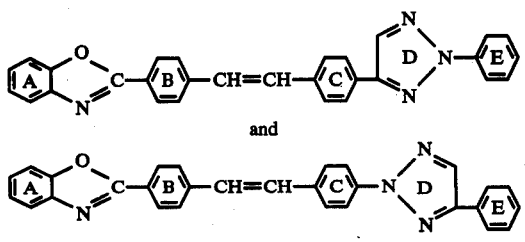

Non-chromophoric substituents are, for example, alkyl with 1 to 12 carbon atoms, cyclohexyl, phenylalkyl with 1 to 3 carbon atoms in the alkyl part, unsubstituted phenyl or phenyl substituted by 1 or 2 substituents from the series chlorine, methyl or methoxy, alkoxy with 1 to 4 carbon atoms, unsubstituted phenoxy or phenoxy substituted by 1 or 2 substituents from the series chlorine, methyl or methoxy, chlorine, bromine, cyano, —COOY, wherein Y represents hydrogen, alkyl with 1 to 5 carbon atoms or benzyl, —CONY'(Y$_1$'), wherein Y' represents hydrogen, alkyl with 1 to 6 carbon atoms, hydroxyalkyl with 1 to 4 carbon atoms, alkoxyalkyl with 2 to 8 carbon atoms, phenyl or benzyl and Y$_1$' represents hydrogen, alkyl with 1 to 6 carbon atoms, hydroxyalkyl with 1 to 4 carbon atoms or alkoxyalkyl with 2 to 8 carbon atoms, or Y' and Y$_1$' conjointly with the nitrogen represent a morpholino or piperidino radical, —SO$_2$OY, wherein Y has the abovementioned meaning, —SO$_2$NY'(Y$_1$'), wherein Y' and Y$_1$' have the abovementioned meaning, alkylsulphonyl with 1 to 6 carbon atoms, benzylsulphonyl or unsubstituted phenylsulphonyl or phenylsulphonyl substituted by chlorine or methyl.

Within the framework of the formula (1), compounds of predominant interest are those of the formula

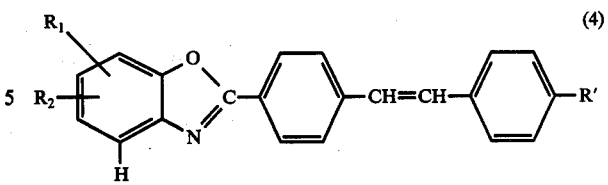

wherein R$_1$ denotes hydrogen, chlorine, alkyl with 1 to 8 carbon atoms, cyclohexyl, phenylalkyl with 1 to 3 carbon atoms in the alkyl part, phenyl or alkoxy with 1 to 4 carbon atoms, R$_2$ denotes hydrogen or alkyl with 1 to 4 carbon atoms and R' denotes a radical

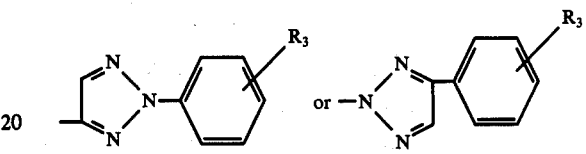

wherein R$_3$ represents hydrogen, alkyl with 1 to 4 carbon atoms, alkoxy with 1 to 4 carbon atoms, chlorine, carbalkoxy with 2 to 5 carbon atoms, unsubstituted sulphamoyl or sulphamoyl which is monosubstituted or disubstituted by alkyl or hydroxyalkyl with 1 to 4 carbon atoms or represents alkylsulphonyl with 1 to 4 carbon atoms.

Accordingly, the formula (4) comprises the compounds of the formulae

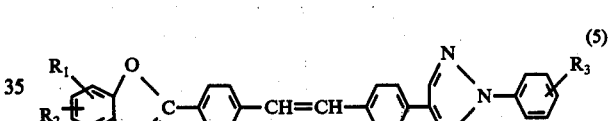

and

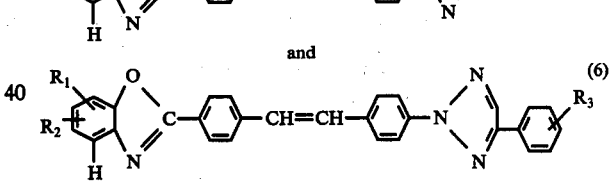

Compounds of particular practical interest within the framework of the formula (4) are the stilbene compounds of the formula

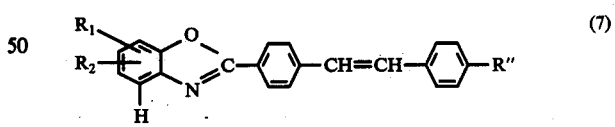

wherein R$_1$ denotes hydrogen, chlorine, alkyl with 1 to 8 carbon atoms, cyclohexyl, phenylalkyl with 1 to 3 carbon atoms in the alkyl part, phenyl or alkoxy with 1 to 4 carbon atoms, R$_2$ denotes hydrogen or alkyl with 1 to 4 carbon atoms and R'' denotes the radical

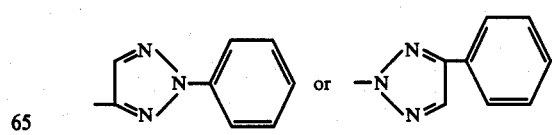

Thus, the formula (7) comprises the compounds of the formulae

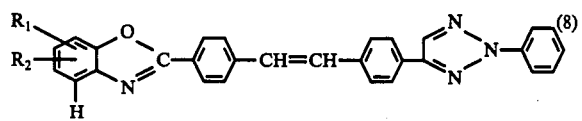

and

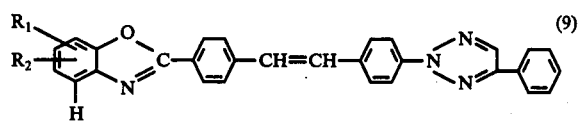

wherein $R_1$ and $R_2$ have the abovementioned meaning.

Compounds to be singled out are those of the formula

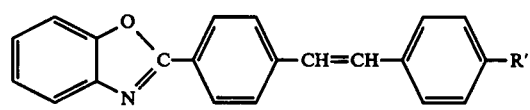

wherein R' denotes a radical

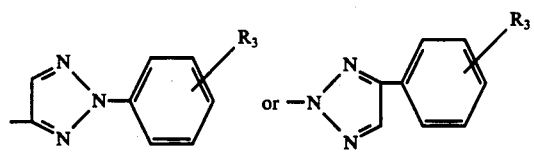

wherein $R_3$ denotes hydrogen, alkyl with 1 to 4 carbon atoms, alkoxy with 1 to 4 carbon atoms, chlorine, carbalkoxy with 2 to 5 carbon atoms, unsubstituted sulphamoyl or sulphamoyl which is monosubstituted or disubstituted by alkyl or hydroxyalkyl with 1 to 4 carbon atoms, or denotes alkylsulphonyl with 1 to 4 carbon atoms.

The formula (10) also comprises the formulae of the two types

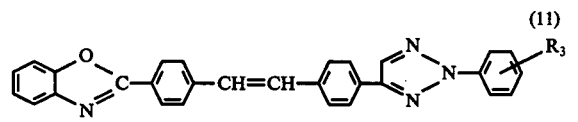

and

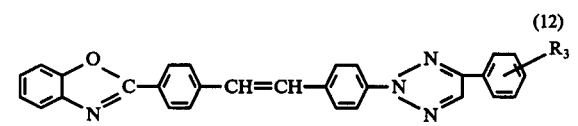

wherein $R_3$ has the abovementioned meaning.

The compounds of the formula

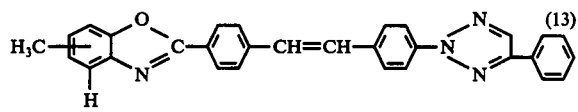

and

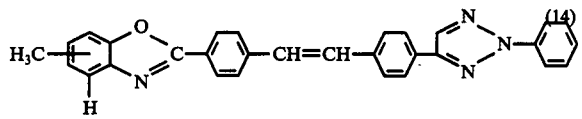

are also worthy of particular mention.

$R_1$ in the formulae (4) to (10) is preferably in the 5-position of the benzoxazole radical, whilst $R_3$ in the formulae (4), (5), (11) and (12) is preferably in the p-position to the bond to the triazole radical.

The compounds of the formula (1) to (14) can be manufactured according to various processes.

New compounds of the formulae (1) to (14) can be manufactured according to a new process which is characterized in that a methyl compound of the formula

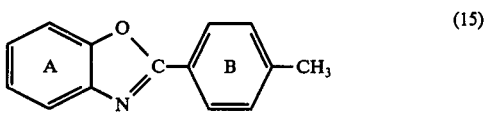

is reacted, in dimethylformamide as the reaction medium and in the presence of a strongly basic alkali metal compound, with a Schiff's base of the formula

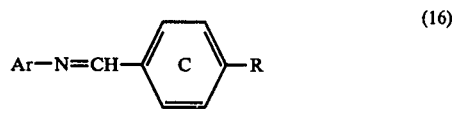

wherein A, B, C and R have the abovementioned meaning and Ar denotes an aromatic radical, the reaction mixture initially being irradiated with UV light.

The irradiation with UV light, according to the invention, is effected by means of a source which is located either outside or inside the reaction vessel. In general, the irradiation with UV light is required only in order to start the reaction, and not constantly until the reaction of the reactants has gone to completion. Therefore, an irradiation time of a few minutes is usually sufficient. Preferably, UV light with a wavelength of above 300 nm is used.

The symbol Ar generally represents an optionally substituted naphthyl or, in particular, phenyl radical. Preferably, Ar represents the radical of the formula

wherein h denotes hydrogen or chlorine.

The strongly basic alkali metal compound used is generally a compound of the formula $$MOC_{n-1}H_{2n-1} \qquad (18)$$

wherein M denotes potassium or sodium and n denotes an integer from 1 to 6.

Examples of compounds of the formula (18) which may be mentioned are sodium methylate, potassium tertiary-butylate, sodium hydroxide and potassium hydroxide.

In the case of alcoholates, the reaction must be carried out in a virtually anhydrous medium, whilst in the case of the hydroxides, water contents of up to 25% are permissible.

In the case of potassium hydroxide, which is preferably to be used, a water content of up to 15% has proved suitable.

Appropriately, the compound containing methyl groups and the Schiff's base are reacted in equivalent amounts so that neither component is present in a substantial excess. Advantageously, at least the equivalent amount of the alkali metal compound is used, that is to say at least 1 mol of alkali metal compound per mol of Schiff's base. When potassium hydroxide is used, two to eight times the equivalent amount is preferably employed.

In general, the reaction according to the invention can be carried out at temperatures in the range between about 10° and 40° C. If potassium hydroxide is used for the reaction, the reaction generally already takes place at room temperature, in which case it is not necessary to supply heat from outside. When other alkali metal compounds are used, the reaction is to be carried out at elevated temperatures, depending on the base strength of the compounds. However, a reaction temperature which is as low as possible is desirable since side reactions, such as, for example, opening of the ring, can occur at higher temperatures.

The end products can be worked up from the reaction mixture according to customary methods which are in themselves known.

Compounds of the formulae (4), (7) and (10) are manufactured analogously by reacting a methyl compound of the formula

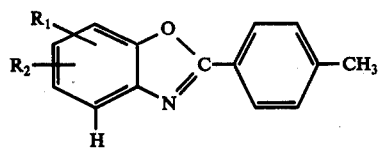 (19)

with a Schiff's base of the formula

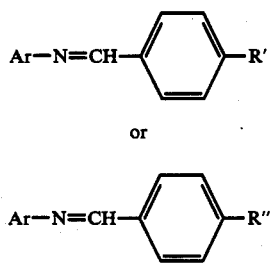 (20)

wherein $R_1$, $R_2$, R', R" and Ar have the abovementioned meanings.

The starting materials of the formulae (15), (16), (19), (20) and (21) are known or are obtained analogously to processes which are in themselves known.

Another process, which is in itself known, for the manufacture of new compounds of the formula (1) is to react a compound of the formula

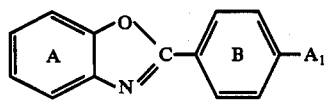 (22)

with a compound of the formula

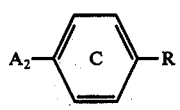 (23)

wherein A, B, C and R have the abovementioned meaning and one of the symbols $A_1$ and $A_2$ denotes a

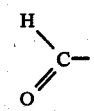

group and the other denotes a grouping of the formula

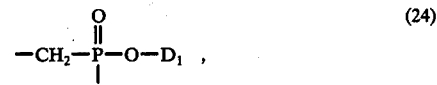 (24)

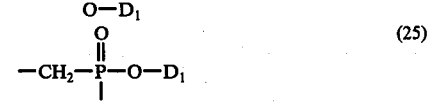 (25)

 (26)

or

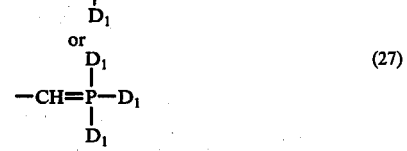 (27)

wherein $D_1$ represents an alkyl radical which is optionally further substituted, preferably an alkyl radical with up to 6 carbon atoms, an aryl radical, preferably a phenyl radical, a cycloalkyl radical, preferably a cyclohexyl radical, or an aralkyl radical, preferably a benzyl radical.

Advantageously, this manufacturing process is carried out in inert solvents. Examples of solvents which may be mentioned are hydrocarbons, such as toluene and xylene, or alcohols, such as methanol, ethanol, isopropanol or butanol, glycols, glycol ethers, such as 2-methoxyethanol, hexanols, cyclohexanol and cyclooctanol and also ethers, such as diisopropyl ether, tetrahydrofurane and dioxane, as well as dimethylsulphoxide, formamide and N-methylpyrrolidone. Polar organic solvents such as dimethylformamide and dimethylsulphoxide are particularly suitable. Some of the reactions can also be carried out in aqueous solution. The temperature at which the reaction is carried out can vary within wide limits. It is determined α. by the stability of the solvent used towards the reactants, especially towards the strongly basic alkali metal compounds, β. by the reactivity of the compounds taking part in the condensation reaction and γ. by the activity of the combination of solvent and base as the condensing agent.

Accordingly, temperatures between about 10° and 100° C can generally be used in practice, especially if dimethylformamide or dimethylsulphoxide is used as the solvent. The preferred temperature range is from 20° to 60° C.

Strongly basic alkali metal compounds which can be used are, above all, the hydroxides, amides and alcoholates (preferably those of primary alcohols containing 1 to 4 carbon atoms) of the alkali metals, those of lithium, sodium and potassium being of predominant interest for economic reasons. However, in principle and in particular cases alkali metal sulphides and alkali metal carbonates, arylalkali metal compounds, such as, for example, phenyl-lithium, or strongly basic amines (including ammonium bases), for example trialkyl-ammonium hydroxides, can also be used successfully.

The compounds of the formulae (2) to (14) are manufactured in an entirely analogous manner, for example those of the formulae (5), (6), (8) and (9) are manufactured by reacting a compound of the formula

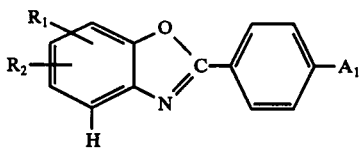
(28)

with a compound of the formula

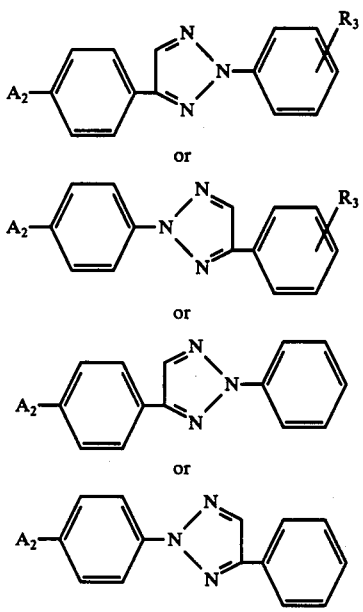
(29)

or (30)

or (31)

or (32)

and those of the formulae (11) and (12) are manufactured by reacting a compound of the formula

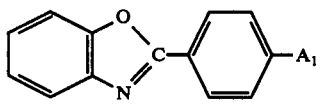
(33)

with a compound of the formula (29) or (30).

The starting materials of the formulae (22), (23) and (28) to (33) are known or are obtained analogously to processes which are in themselves known.

A further analogous process for the manufacture of compounds of the formula (1), (4), (7) and (10) is to react an aminophenol of the formula

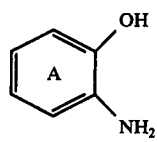
(34)

in a first stage with a compound of the formula

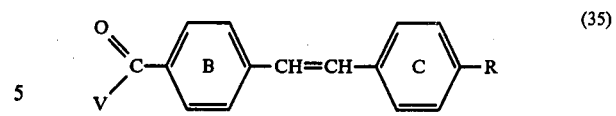
(35)

wherein A, B, C and R have the abovementioned meaning and V denotes hydroxyl, alkoxy with 1 to 4 carbon atoms or chlorine, to give an acyl compound of the formula

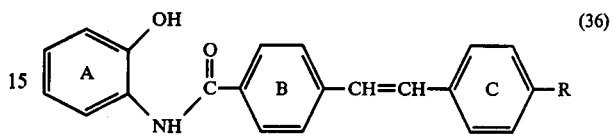
(36)

and then to convert this by heating to temperatures above 100° C, optionally in the presence of a catalyst, into compounds of the formula (1).

The new compounds of the formula (35) can be manufactured according to the procedure which is in itself known and has already been described above and which is characterised by the reaction of a compound of the formula

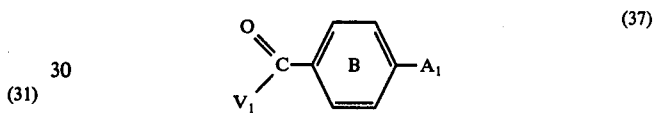
(37)

wherein $V_1$ denotes hydroxyl or alkyl with 1 to 4 carbon atoms, with a compound of the formula (23).

The new compounds defined above show a more or less pronounced fluorescence in the dissolved or finely divided state. They can be used for the optical brightening of the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high molecular materials:
  a. Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacryl analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride),
  b. Polymerisation products such as are obtainable by ring opening, for example polyamides of the polycaprolactam type, and also polymers which are obtainable both via polyaddition and via polycondensation, such as polyethers or polyacetals.

c. Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, such as, for example, alkyd resins) polyesters, polyamides (for example hexamethylenediamine adipate), maleate resins, melamine resins, their precondensates and analogues, polycarbonates and silicones, d. Polyaddition products such as polyurethanes (crosslinked and non-crosslinked) and epoxide resins.

II. Semi-synthetic organic materials, for example cellulose esters of varying degrees of esterification (so-called 2½ acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, foils, lacquers, coatings, impregnations and coverings, or as predominantly one-dimensional bodies such as filaments, fibers, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fiber materials can, for example, be in the form of endless filaments (stretched or unstretched), staple fibers, flocks, hanks, textile filaments, yarns, threads, fiber fleeces, felts, waddings, flocked structures or woven textile fabrics, textile laminates, knitted fabrics and papers, cardboards or paper compositions.

The compounds to be used according to the invention are of importance, inter alia, for the treatment of organic textile materials, especially woven textile fabrics. Where fibers, which can be in the form of stable fibers or endless filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brightening agents according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brightening agents according to the present invention can, for example, also be employed in the following use forms:

a. Mixtures with dyestuffs (shading) or pigments (coloured pigments or especially, for example, white pigments), or as an additive to dye baths, printing pastes, discharge pastes or reserve pastes, and also for the after-treatment of dyeings, prints or discharge prints.

b. Mixed with so-called "carriers", wetting agents, plasticisers, swelling agents, andi-oxidants, light protection agents, heat stabilisers and chemical bleaching agents (chlorite bleach or bleaching bath additives).

c. mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches".

f. As additives to the most diverse industrial products in order to render these more marketable (for example improving the appearance of soaps, detergents, pigments), g. In combination with other optically brightening substances, h. In spinning bath preparations, that is to say as additives to spinning bths such as are used for improving the slip for the further processing of synthetic fibers, or from a special bath before the stretching of the fiber.

i. As scintillators for various purposes of a photographic nature, such as, for example, for electrophotographic reproduction of supersensitisation, and for the optical brightening of photographic layers, optionally in combination with white pigments such as, for example TiO₂.

k. Depending in each case on the substituents, as laser dyestuffs.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fiber substrates, for example of polyester fibers, with the brighteners according to the invention is to impregnate these fibers with the aqueous dispersions (or optionally also solutions) of the brightening agents at temperatures below 75° C, for example at room temperature, and to subject them to a dry heat treatment at temperatures above 100° C, it being generally advisable additionally to dry the fiber material beforehand at a moderately elevated temperature, for example at not less than 60° C and up to about 130° C. The heat treatment in the dry state is then advantageously carried out at temperatures between 120° and 225° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.001 percent by weight. However, amounts of up to about 0.8 percent by weight and optionally of up to about 2 percent by weight can also be employed. For most practical purposes, amounts btween 0.01 and 0.5 percent by weight are of preferred interest.

The new optical brightening agents are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, synthetic, soluble salts of sulphonic acid half esters or higher fatty alcohols, arylsulphonic acids with higher and/or multiple alkyl substituents, sulphocarboxylic acid esters of medium to higher alcohols, fatty acid acylaminoalkyl- or acylaminoaryl-glycerol sulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The washing agents can further contain, for example: antistatic agents, skin protection agents which restore fat, such as lanolin, enzymes, anti-microbial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of cellulose fibers, polyamide fibers, cellulose fibers with a high quality finish, polyester fibers, wool and the like.

The washing treatment is carried out as follows, for example:

The textiles indicated are treated for 1 to 30 minutes at 20° to 100° C in a wash liquor which contains 1 to 10 g/kg of a built-up composite washing agent and 0.05 to 1%, relative to the weight of the washing agent, of the claimed brightening agents. The liquor ratio can be 1:3 to 1:50. After washing, the textiles are rinsed and dried in the usual manner. The wash liquor can contain 0.2 g/l of active chlorine (for example as hypochlorite) or 0.1 to 2 g/l of sodium perborate as a bleaching additive.

In the examples the parts, unless otherwise stated, are always parts by weight and the percentages are always percentages by weight. Unless othewise noted, melting points and boiling points are uncorrected.

EXAMPLE 1

3.57 g (0.0125 mol) of 2-(p-tolyl)-5-phenyl-benzoxazole of the formula

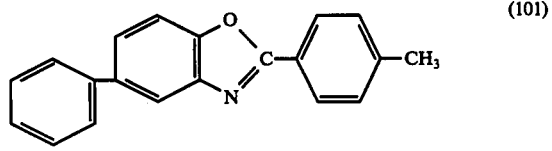

(101)

and 4.48 g (0.0125 mol) of the Schiff's base, obtained from 2-phenyl-4-(p-formylphenyl)-2H-1,2,3-triazole and o-chloroaniline, of the formula

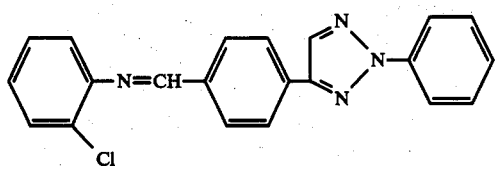 (102)

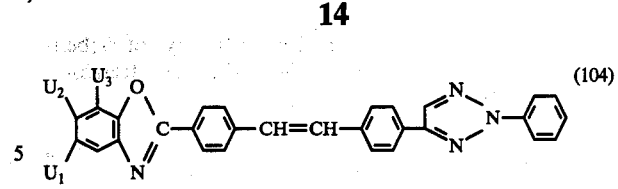 (104)

which are listed in the table which follows can be prepared in an analogous manner:

TABLE I

| No. | $U_1$ | $U_2$ | $U_3$ | Melting point ° C |
|---|---|---|---|---|
| 105 | H | H | H | 233 – 234 |
| 106 | —CH$_3$ | H | H | 219 – 220 |
| 107 | H | —CH$_3$ | H | 228 – 229 |
| 108 | H | H | —CH$_3$ | 181 – 181,5 |
| 109 | —CH$_3$ | —CH$_3$ | H | 257 – 258 |
| 110 | —CH$_3$ | H | —CH$_3$ | 204 – 205 |
| 111 | —C$_2$H$_5$ | H | H | 258 – 259 |
| 112 | —CH$_2$CH$_2$CH$_3$ | H | H | 262 – 263 |
| 113 | —CH(CH$_3$)$_2$ | H | H | 236 – 237 |
| 114 | —C(CH$_3$)$_3$ | H | H | 253 – 254 |
| 115 | —CH$_3$ | H | —C(CH$_3$)$_3$ | 252 – 253 |
| 116 | —C(CH$_3$)$_3$ | H | —CH$_3$ | 216 – 217 |
| 117 | $\begin{array}{c}\text{H}_3\text{C} \quad \text{CH}_3 \\ \mid \quad\quad \mid \\ -\text{C}-\text{CH}_2-\text{C}-\text{CH}_3 \\ \mid \quad\quad \mid \\ \text{H}_3\text{C} \quad \text{CH}_3\end{array}$ | H | H | 222 – 223 |
| 118 | —CH$_2$—C$_6$H$_5$ | H | H | 226 – 227 |
| 119 | $\begin{array}{c}\text{CH}_3 \\ \mid \\ -\text{C}-\text{C}_6\text{H}_5 \\ \mid \\ \text{CH}_3\end{array}$ | H | H | 207 – 208 |
| 120 | cyclohexyl-H | H | H | 273 – 274 |
| 121 | H | C$_6$H$_5$ | H | 276 – 277 |
| 122 | OCH$_3$ | H | H | 238 – 239 |
| 123 | Cl | H | H | 250 – 251 |

(melting point: 109.5 to 110° C) and 3.15 g (~0.05 mol) of powdered potassium hydroxide with a water content of about 10% are stirred in 80 ml of dimethylformamide for one hour at 20° to 25° C, under nitrogen. During the first 10 minutes of the reaction, the reaction mixture is irradiated with UV light of wavelength above 300 nm. The colour of the reaction mixture gradually changes from yellow via red-brown to red-violet. Thereafter, 400 ml of methanol are added and the mixture is cooled to 0° C. The product which has precipitated is filtered off, washed by covering several times with a total of 150 ml of methanol and dried. 5.5 g (corresponding to 84.1% of theory) of 4-(5-phenyl-benzoxazol-2-yl)-4'-(2-phenyl-2H-1,2,3-triazol-4-yl)-stilbene of the formula

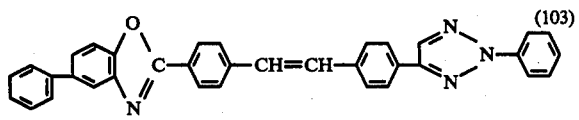 (103)

are obtained as a beige-yellow powder. After recrystallisation from o-dichlorobenzene (bleaching earth) and then from dimethylformamide, 4.0 g (77.4% of theory) of small light greenish-tinged yellow shiny needles and flakes of melting point 276° to 277° C are obtained.

Analysis: C$_{35}$H$_{24}$N$_4$O (516.57); calculated: C 81.37; H 4.68; N 10.85; found: C 81.41; H 4.83; N 11.00.

The compounds of the formula

EXAMPLE 2

5.6 g (0.02 mol) of 2-(p-methoxyphenyl)-4-(p-formylphenyl)-2H-1,2,3-triazole of the formula

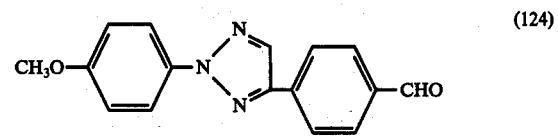 (124)

(Melting point: 150° C)
and 7.6 g (0.022 mol) of 2-(p-diethylphosphono-methylphenyl)-benzoxazole of the formula

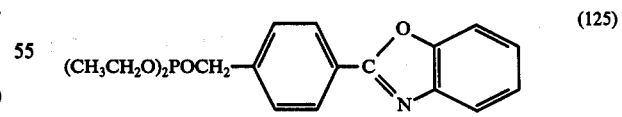 (125)

(Melting point: 88° C)
are warmed to 40° C in 150 ml of dimethylformamide. 1.4 g (0.026 mol) of sodium methylate are now introduced in portions into the solution in the course of 30 minutes and the suspension which is formed is stirred for a further 4 hours at 40° C. The reaction mixture is discharged into water and the precipitate is filtered off and washed with water and then with a total of 120 ml of methanol. The product is recrystallised from chlorobenzene, bleaching earth being added.

8.1 g (corresponding to 87.5% of theory) of 4-(benzoxazol-2-yl)-4′-(2-p-methoxyphenyl-2H-1,2,3-triazol-4-yl)-stilbene of the formula

     (126)

are obtained as small beige-yellow shiny flakes of melting point 255° C.

Analysis: $C_{30}H_{24}N_4O_2$ (472.52);
calculated: C 76.25; H 5.12; N 11.86;
found: C 76.06; H 4.90; N 11.90.

The compounds of the formula

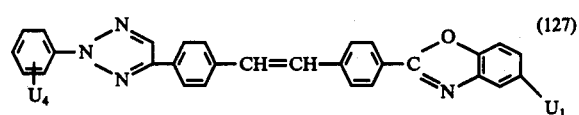     (127)

which are listed in Table II which follows can be prepared in an analogous manner:

TABLE II

| No. | $U_1$ | $U_4$ | Melting point °C |
|---|---|---|---|
| 105 | H | H | 240 |
| 128 | H | p-SO$_2$CH$_3$ | > 330 |
| 129 | H | o-OCH$_3$ | 240–243 |
| 130 | H | p-Cl | 280 |
| 131 | H | p-COOCH$_3$ | 279 |
| 132 | H | p-SO$_2$NH$_2$ | >330 |
| 133 | —COOCH$_3$ | H | >300 |
| 134 | —CH$_2$CH$_2$CN | H | >300 |
| 135 | —SO$_2$C$_6$H$_5$ | H | 271–272 |
| 136 | —SO$_2$CH$_3$ | H | 262–263 |

The compounds of the formulae (105), (126), (128), (129), (130), (131) and (132) can also be manufactured analogously starting from 2-aryl-4-(p-diethylphosphonomethylphenyl)-2H-1,2,3-triazoles of the formula

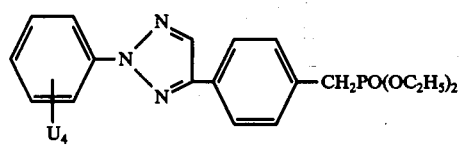     (137)

and 2-(p-formylphenyl)-benzoxazole of the formula

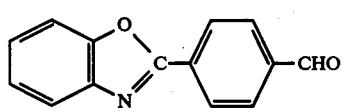     (138)

2-Phenyl-4-(p-formylphenyl)-2H-1,2,3-triazole of the formula

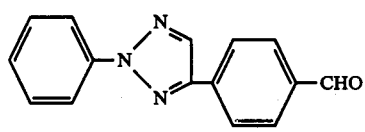     (139)

which is used as the starting material for the manufacture of the compound of the formula (105), can be prepared as follows:

5.7 g (0.065 mol) of 2-nitropropane are introduced at about 20° C into a solution of 1.15 g (0.05 mol) of sodium in 1,000 ml of ethanol. The reaction mixture is stirred for one hour and warmed to 35° C and 16.0 g (0.05 mol) of 2-phenyl-4-(p-bromoethylphenyl)-2H-1,2,3-triazole are now added. The solution is then stirred for 20 hours without heating form outside, the suspension formed is filtered and the filter cake is washed with water until neutral. A further amount of the product can be obtained by concentrating the mother liquor. After recrystallisation from ethanol, 8.9 g (corresponding to 69.5% of theory) of the compound of the formula (139) are obtained as a white crystalline powder of melting point 149° C.

The aldehydes of the formula

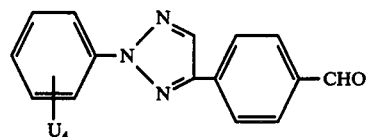     (140)

which are listed in Table III can be manufactured according to the same process:

TABLE III

| No. | $U_4$ | Melting point: °C |
|---|---|---|
| 141 | p-SO$_2$CH$_3$ | 210 |
| 142 | p-OCH$_3$ | 150 |
| 143 | o-OCH$_3$ | 147 |
| 144 | p-Cl | 130 |
| 145 | p-COOCH$_3$ | 120 |
| 146 | p-SO$_2$NH$_2$ | 250 |

The compound of the formula

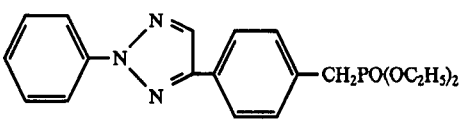     (147)

is manufactured as follows:

100 ml of triethyl phosphite are warmed to 120° C and 16.0 g (0.05 mol) of 2-phenyl-4-(p-bromomethylphenyl)-2H-1,2,3-triazole are then added in portions in the course of 10 minutes, the turbid solution is stirred for 3 hours at 130° C and the excess triethyl phosphite is then distilled off in vacuo. The residue solidifies on standing. The crude product (19.3 g) is finely triturated with hexane in a mill, then filtered off and recrystallised from a solvent mixture of hexane and benzene. 17.7 g (corresponding to 93.5% of theory) of the compound of the formula (147) are obtained as a white crystalline powder of melting point 102° to 103° C.

EXAMPLE 3

3.8 g (0.015 mol) of 2-(p-formylphenyl)-4-phenyl-2H-1,2,3-triazole of the formula

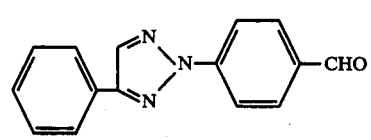     (148)

(melting point: 149° C)
and 5.3 g (0.015 mol) of 2-(p-diethylphosphonomethylphenyl)-benzoxazole of the formula

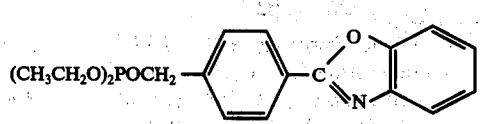
(125)

(melting point: 88° C)
are warmed to 40° C in 25 ml of dimethylformamide. 1.2 g (0.023 mol) of sodium methylate are now introduced in portions into the solution in the course of 20 minutes and the yellow suspension formed is stirred for a further 3 hours at 40° C. The product which has precipitated is filtered off and suspended in 70 ml of hot water, the suspension is filtered hot and the residue is washed by covering several times with a total of 150 ml of methanol and dried. 7.0 g (corresponding to 74.5% of theory) of the compound of the formula

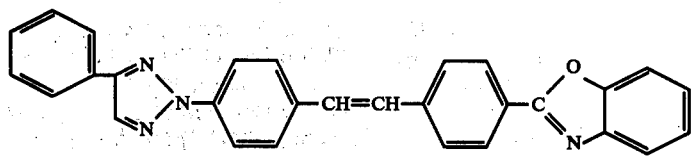
(149)

are obtained as small light yellow-green plates of melting point 259° to 260° C. After recrystallisation from dimethylformamide (active charcoal), the following analytical values are obtained.
$C_{29}H_{20}N_4O$ (440.48);
calculated: C 79.07; H 4.58; N 12.72;
found: C 79.05; H 4.50; N 12.64.
The compounds of the formula

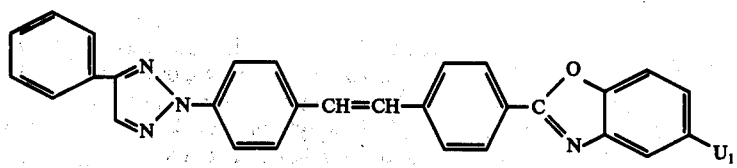
(150)

which are listed in Table IV which follows can be prepared in an analogous manner:

TABLE IV

| No. | U₁ | Melting point: °C |
|---|---|---|
| 151 | —SO₂CH₃ | 275 |
| 152 | —CH₂CH₂CN | > 300 |

2-(p-Diethylphosphonomethyl-phenyl)-benzoxazoles of the formula

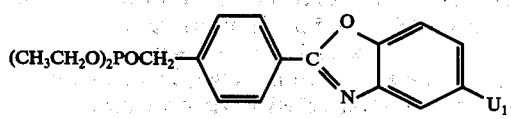
(153)

which are required for the manufacture of the compounds (133) to (136), (151) and (152), can be manufactured analogously to compound (147) from the corresponding bromomethyl compounds using triethyl phosphate. See Table V for the melting points.

TABLE V

| No. | U₁ | Melting point : °C |
|---|---|---|
| 154 | —COOCH₃ | 98 – 101 |
| 155 | —CH₂CH₂CN | 88 – 90 |
| 156 | —SO₂C₆H₅ | 105 – 107 |
| 157 | —SO₂CH₃ | 133 – 134 |

EXAMPLE 4

2.65 g (0.01 mol) of 2-(p-tolyl)-5-tert. butylbenzoxazole of the formula (158)

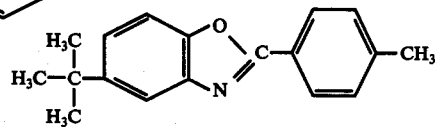

and 3.59 g (0.01 mol) of the Schiff's base, obtained from 4-phenyl-2-(p-formylphenyl)-2H-1,2,3-triazole and o-chloroaniline, of the formula (159)

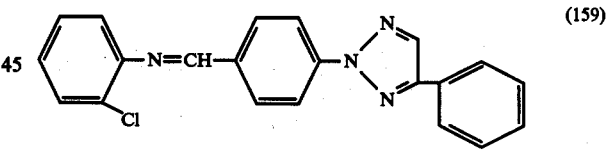

(melting point: 120.5° to 121° C) and 2.5 g (~0.04 mol) of powdered potassium hydroxide with a water content of about 10% are stirred in 80 ml of dimethylformamide for one hour at 20° to 30° C, under nitrogen. During the first 10 minutes of the reaction, the reaction mixture is irradiated with UV light of wavelengths above 300 nm. Working up is analogous to Example 1. 4.08 g (82.3% of theory) of 4-(5-tert.-butylbenzoxazol-2-yl)-4'-(4-phenyl-2H-1,2,3-triazol-2-yl)-stilbene of the formula (160)

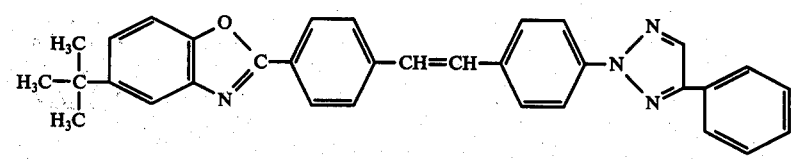

are obtained as a light yellow powder of melting point 230° to 231° C. After recrystallising twice from toluene (bleaching earth), 3.6 g (72.6% of theory) of small light greenish-tinged yellow, matted needles of melting point 231° to 232° C are obtained.

Analysis: $C_{33}H_{28}N_4O$ (496.59);
calculated: C 79.81; H 5.68; N 11.28%;
found: C 79.79; H 5.85; N 11.30%.

The compounds of the formula

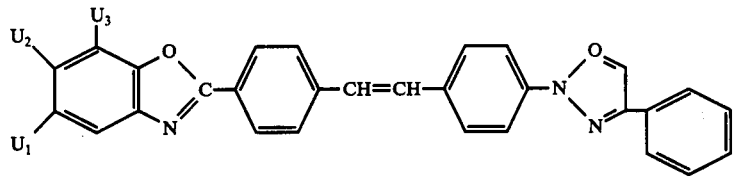

which are listed in Table VI which follows, can be prepared in an analogous manner:

TABLE VI

| No. | $U_1$ | $U_2$ | $U_3$ | Melting point ° C |
|---|---|---|---|---|
| 149 | H | H | H | 256–257 |
| 162 | —CH₃ | H | H | 232–233 |
| 163 | H | —CH₃ | H | 230–231 |
| 164 | H | H | —CH₃ | 225–226 |
| 165 | —CH₃ | —CH₃ | H | 243–244 |
| 166 | —CH₃ | H | —CH₃ | 182,5–183 |
| 167 | —CH₂—CH₂—CH₃ | H | H | 195–195,5 |
| 168 | —CH(CH₃)₂ | H | H | 218–219 |
| 169 | —C(CH₃)₃ | H | —CH₃ | 165–165,5 |
| 170 | —CH₃ | H | —C(CH₃)₃ | 225–226 |
| 171 | —OCH₃ | H | H | 228–229 |
| 172 | —C₆H₅ | H | H | 279–280 |
| 173 | H | —C₆H₅ | H | 286–287 |

EXAMPLE 5

Polyester fabric (25 g) is introduced, using a liquor ratio of 1:40, into a bath which contains, per liter, 10 g of a condensation product of aromatic sulphonic acids, 25 g of an aromatic carboxylic acid ester as the emulsifier and 5 g of sodium dihydrophosphate and the pH value of which has been adjusted to 5 using acetic acid. After a dyeing time of one hour at the boil in the presence of 0.05 g/l of a brightener of the formulae (103), (105) to (123), (126), (128) to (132), (134), (149) or (162) to (173), the fabric displays a brilliant brightening effect of good fastness to light.

EXAMPLE 6

0.01 percent by weight of a brightener of the formulae (103), (105) to (123) is milled into opaque soft polyvinyl chloride. The polyvinyl chloride displays a neutral white brightening effect of good fastness to light.

EXAMPLE 7

100 parts of polyester granules consisting of terephthalic acid ethylene glycol polyester are intimately mixed with 0.05 part of one of the compounds of the formulae (103), (105) to (123), (126), (128) to (132), (134), (149) or (162) to (173) and the mixture is melted at 285° C whilst stirring. After the spinning melt has been spun out through customary spinnerets, strongly brightened polyester fibers of good fastness to light are obtained.

The abovementioned compounds can also be added to the starting materials before or during the polycondensation to give the polyester.

EXAMPLE 8

A polyester fabric (for example "DACRON") is padded at room temperature (about 20° C) with an aqueous dispersion, which contains, per liter, 2 g of one of the compounds of the formulae (103), (105) to (123), (126), (128) to (132), (149) or (162) to (173) as well as 1 g of a product of the addition reaction of about 8 mols of ethylene oxide with 1 mol of p-tert.-octylphenol, and (161)

dried at about 100° C. The dry material is then subjected to a heat treatment at 170° to 220° C, the treatment time being from 2 minutes down to a few seconds, depending on the temperature. The material treated in this way displays a strong brightening effect of good fastness to light.

What we claim is:

1. Stilbene compounds of the formula

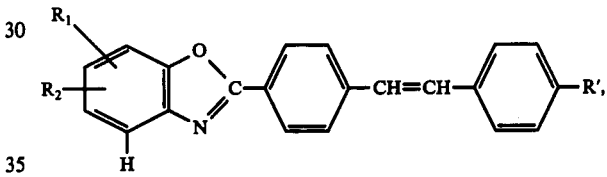

wherein $R_1$ denotes hydrogen, chlorine, alkyl with 1 to 8 carbon atoms, alkoxy with 1 to 4 carbon atoms, alkoxycarbonyl with 1 to 4 carbon atoms in the alkoxy rest, cyanoalkyl, alkylsulphonyl, phenylalkyl with 1 to 3 carbon atoms in the alkyl part, sulfamoyl, cyclohexyl, phenyl, phenylsulphonyl or benzyl, $R_2$ denotes hydrogen or alkyl with 1 to 4 carbon atoms and R' denotes a radical

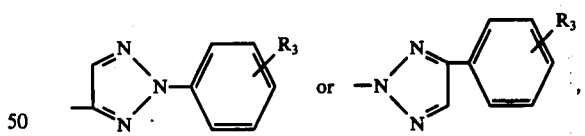

wherein $R_3$ represents hydrogen, chlorine, alkyl with 1 to 4 carbon atoms, alkoxy with 1 to 4 carbon atoms, carbalkoxy with 2 to 5 carbon atoms, unsubstituted sulphamoyl or sulphamoyl which is monosubstituted or disubstituted by alkyl or hydroxyalkyl with 1 to 4 carbon atoms or represents alkylsulphonyl with 1 to 4 carbon atoms.

2. Stilbene compounds according to claim 1, of the formula

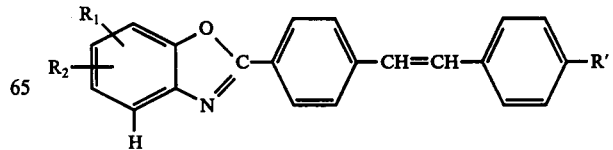

wherein R₁ denotes hydrogen, chlorine, alkyl with 1 to 8 carbon atoms, cyclohexyl, phenylalkyl with 1 to 3 carbon atoms in the alkyl part, phenyl or alkoxy with 1 to 4 carbon atoms, R₂ denotes hydrogen or alkyl with 1 to 4 carbon atoms and R' denotes a radical

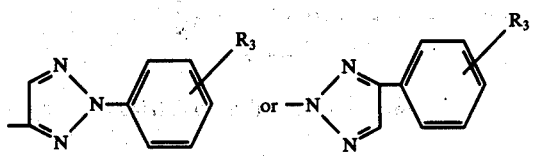

wherein R₃ represents hydrogen, alkyl with 1 to 4 carbon atoms, alkoxy with 1 to 4 carbon atoms, chlorine, carbalkoxy with 2 to 5 carbon atoms, unsubstituted sulphamoyl or sulphamoyl which is monosubstituted or disubstituted by alkyl or hydroxyalkyl with 1 to 4 carbon atoms or represents alkylsulphonyl with 1 to 4 carbon atoms.

3. Stilbene compounds according to claim 2, of the formula

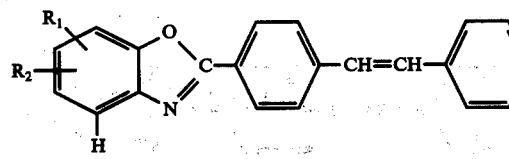

wherein R₁ denotes hydrogen, chlorine, alkyl with 1 to 8 carbon atoms, cyclohexyl, phenylakyl with 1 to 3 carbon atoms in the alkyl part, phenyl or alkoxy with 1 to 4 carbon atoms, R₂ denotes hydrogen or alkyl with 1 to 4 carbon atoms and R" denotes the radical

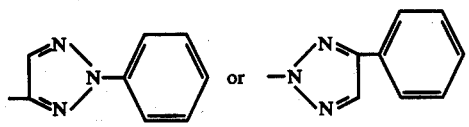

4. Stilbene compounds according to claim 3, of the formula

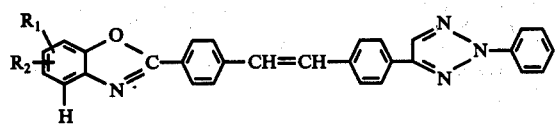

wherein R₁ denotes hydrogen, chlorine, alkyl with 1 to 8 carbon atoms, cyclohexyl, phenylakyl with 1 to 3 carbon atoms in the alkyl part, phenyl or alkoxy with 1 to 4 carbon atoms and R₂ denotes hydrogen or alkyl with 1 to 4 carbon atoms.

5. Stilbene compounds according to claim 3 of the formula

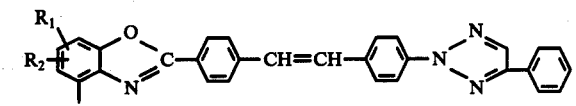

wherein R₁ denotes hydrogen, chlorine, alkyl with 1 to 8 carbon atoms, cyclohexyl, phenylakyl with 1 to 3 carbon atoms in the alkyl part, phenyl or alkoxy with 1 to 4 carbon atoms and R₂ denotes hydrogen or alkyl with 1 to 4 carbon atoms.

6. Stilbene compounds according to claim 2 of the formula

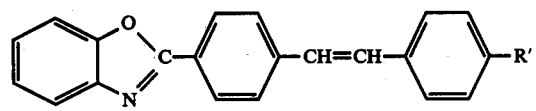

wherein R' denotes a radical

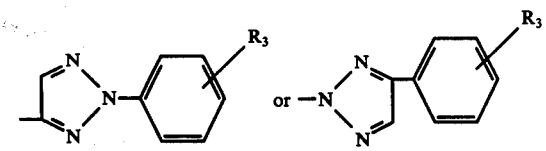

wherein R₃ denotes hydrogen, alkyl with 1 to 4 carbon atoms, alkoxy with 1 to 4 carbon atoms, chlorine, carbalkoxy with 2 to 5 carbon atoms, unsubstituted sulphamoyl or sulphamoyl which is monosubstituted or disubstituted by alkyl or hydroxyalkyl with 1 to 4 carbon atoms or denotes alkylsulphonyl with 1 to 4 carbon atoms.

7. Stilbene compounds according to claim 6 of the formula

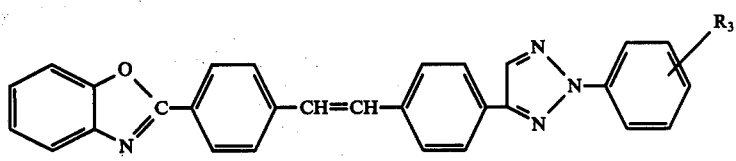

wherein R₃ denotes hydrogen, alkyl with 1 to 4 carbon atoms, alkoxy with 1 to 4 carbon atoms, chlorine, carbalkoxy with 2 to 5 carbon atoms, unsubstituted sulphamoyl or sulphamoyl which is monosubstituted or disubstituted by alkyl or hydroxyalkyl with 1 to 4 carbon atoms or denotes alkylsulphonyl with 1 to 4 carbon atoms.

8. Stilbene compounds according to claim 6 of the formula

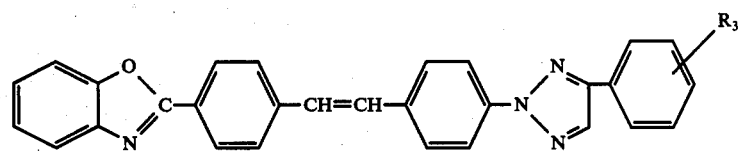

where R₃ denotes hydrogen, alkyl with 1 to 4 carbon atoms, alkoxy with 1 to 4 carbon atoms, chlorine, carbalkoxy with 2 to 5 carbon atoms, unsubstituted sulphamoyl or sulphamoyl which is monosubstituted or disubstituted by alkyl or hydroxyalkyl with 1 to 4 carbon atoms or denotes alkylsulphonyl with 1 to 4 carbon atoms.

9. Stilbene compounds according to claim 3 of the formula

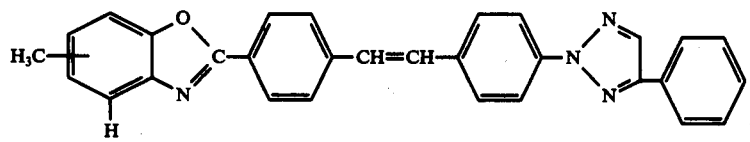

10. Stilbene compounds according to claim 3 of the formula

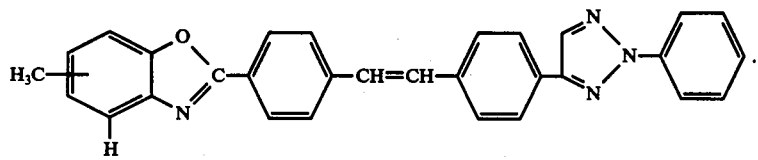

11. The compound according to claim 10 of the formula

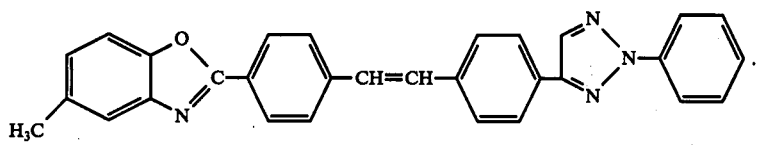

12. The compound according to claim 10 of the formula

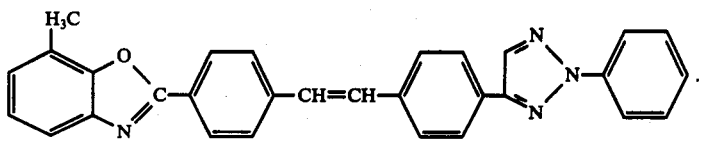

13. The compound according to claim 3 of the formula

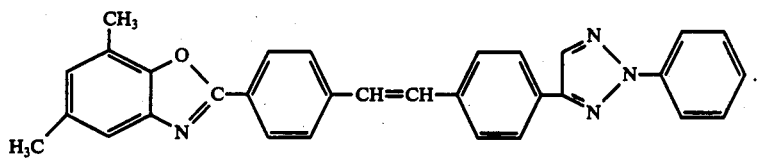

14. The compound according to claim 5 of the formula

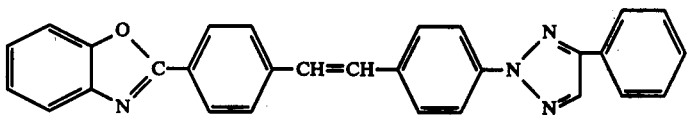

15. The compound according to claim 4 of the formula

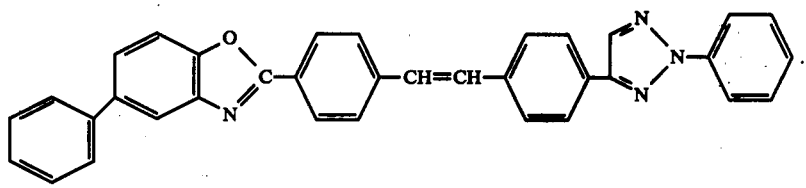

16. Process for the manufacture of stilbene compounds of the formula

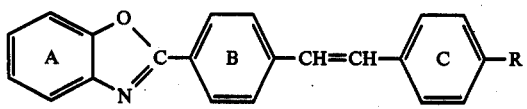

wherein R denotes the radical

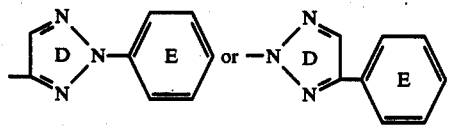

and wherein the rings, A, B, C, D and E can possess nonchromophoric substituents selected from the group consisting of chlorine, alkyl with 1 to 8 carbon atoms, alkoxy with 1 to 4 carbon atoms, alkoxycarbonyl with 1 to 4 carbon atoms in the alkoxy rest, cyanoalkyl, alkylsulphonyl with 1 to 4 carbon atoms in the alkyl rest, phenylalkyl with 1 to 3 carbon atoms in the alkyl part, sulfamoyl, cyclohexyl, phenyl, phenylsulphonyl or benzyl, which comprises reacting a methyl compound of the formula

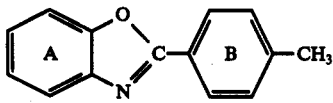

in dimethylformamide as the reaction medium and in the presence of a strongly basic alkali metal compound, with a Schiff's base of the formula

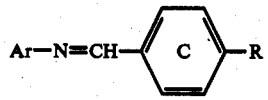

wherein A, B, C and R have the abovementioned meaning and Ar denotes an aromatic radical, the reaction mixture being irradiated with an effective amount of UV light to initiate the reaction.

17. Process according to claim 16 for the manufacture of stilbene compounds of the formula

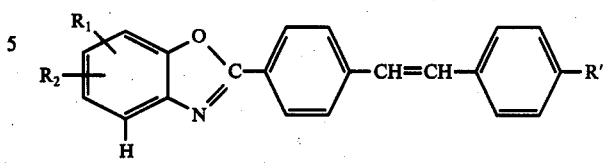

wherein $R_1$ denotes hydrogen, chlorine, alkyl with 1 to 8 carbon atoms, cyclohexyl, phenylalkyl with 1 to 3 carbon atoms in the alkyl part, phenyl or alkoxy with 1 to 4 carbon atoms, $R_2$ denotes hydrogen or alkyl with 1 to 4 carbon atoms and R' denotes a radical

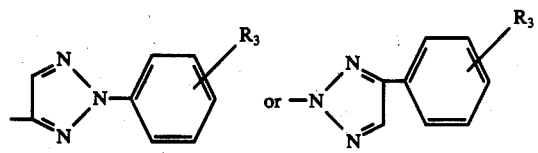

wherein $R_3$ denotes hydrogen, m-methyl, alkyl with 2 to 4 carbon atoms, alkoxy with 1 to 4 carbon atoms, chlorine or alkylsulphonyl with 1 to 4 carbon atoms, which comprises reacting a methyl compound of the formula

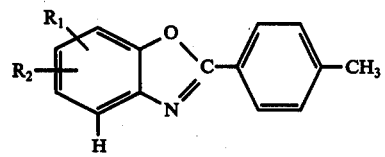

is reacted with a Schiff's base of the formula

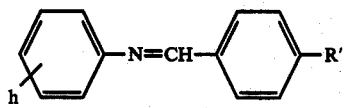

wherein $h$ denotes hydrogen or chlorine.

18. Process according to claim 16, which comprises using in that potassium hydroxide as the strongly basic alkali metal compound and the reaction mixture is irradiated with UV light of wavelenghts above 300 nm.

* * * * *